(12) United States Patent
Westenfelder et al.

(10) Patent No.: US 12,281,330 B2
(45) Date of Patent: Apr. 22, 2025

(54) ADAPTATION OF HOLLOW-FIBER-BASED CELL CULTURE TECHNOLOGY FOR THE MANUFACTURING OF (1) NEO-ISLETS, EMPLOYED FOR THE TREATMENT OF TYPE 1 AND TYPE 2 DIABETES MELLITUS, AND (2) THE GENERATION OF EXOSOMES FROM VARIOUS CELL TYPES, USED IN THE TREATMENT OF DIFFERENT ORGAN INJURIES AND DISEASES

(71) Applicant: SYMBIOCELLTECH, LLC, Salt Lake City, UT (US)

(72) Inventors: Christof Westenfelder, Salt Lake City, UT (US); Anna L. Gooch, Salt Lake City, UT (US)

(73) Assignee: SymbioCellTech, Salt Lake City, UT (US)

(*) Notice: Subject to any disclaimer, the term of this patent is extended or adjusted under 35 U.S.C. 154(b) by 658 days.

(21) Appl. No.: 16/646,112

(22) PCT Filed: Sep. 7, 2018

(86) PCT No.: PCT/US2018/049950
§ 371 (c)(1),
(2) Date: Mar. 10, 2020

(87) PCT Pub. No.: WO2019/051225
PCT Pub. Date: Mar. 14, 2019

(65) Prior Publication Data
US 2020/0208115 A1    Jul. 2, 2020

Related U.S. Application Data

(60) Provisional application No. 62/556,888, filed on Sep. 11, 2017.

(51) Int. Cl.
| | | |
|---|---|---|
| *C12N 5/00* | (2006.01) | |
| *A61P 3/10* | (2006.01) | |
| *C12M 1/00* | (2006.01) | |
| *C12N 5/071* | (2010.01) | |
| *C12N 5/0775* | (2010.01) | |

(52) U.S. Cl.
CPC ............. *C12N 5/0667* (2013.01); *A61P 3/10* (2018.01); *C12M 29/10* (2013.01); *C12N 5/0676* (2013.01); *C12N 2521/00* (2013.01)

(58) Field of Classification Search
CPC . C12N 2521/00; C12N 5/0676; C12N 5/0667
See application file for complete search history.

(56) References Cited

U.S. PATENT DOCUMENTS

| | | | | |
|---|---|---|---|---|
| 6,815,203 B1* | 11/2004 | Bonner-Weir | ....... | C12N 5/0676 435/375 |
| 2012/0308531 A1 | 12/2012 | Pinxteren et al. | | |
| 2015/0076066 A1 | 3/2015 | Zink et al. | | |

FOREIGN PATENT DOCUMENTS

| | | |
|---|---|---|
| WO | 2016177859 A1 | 11/2016 |
| WO | 2017023689 A1 | 2/2017 |
| WO | 2017117585 A1 | 7/2017 |
| WO | 2017122095 A1 | 7/2017 |

OTHER PUBLICATIONS

Hasilo, et al. "Presence of Diabetes Autoantigens in Extracellular Vesicles Derived from Human Islets." Scientific Reports, vol. 7, No. 1, 2017, p. 5000.
Krishnan, Rahul, et al. "Islet and Stem Cell Encapsulation for Clinical Transplantation." The Review of Diabetic Studies : RDS, vol. 11, No. 1, 2014, pp. 84-101.
PCT International Search Report and Written Opinion for International Application No. PCT/US2018/049950 Applicant Symbiocelltech, LLC, international filing date Sep. 7, 2018, date of mailing Jan. 16, 2019, 20 pgs.
Shabbir, Arsalan, et al. "Mesenchymal Stem Cell Exosomes Induce Proliferation and Migration of Normal and Chronic Wound Fibroblasts, and Enhance Angiogenesis in Vitro." Stem Cells and Development, vol. 24, No. 14, 2015, pp. 1635-1647.
Storm, Michael P, et al. "Hollow Fiber Bioreactors for In Vivo-like Mammalian Tissue Culture." Journal of Visualized Experiments, vol. 2016, No. 111, 2016, pp. Journal of Visualized Experiments, May 2016, Issue 111, pp. 1-12.
Tapia et al., "Bioreactors for high cell density and continuous multi-stage cultivations: options for process Intensification in cell culture-based viral vaccine production." Applied Microbioogy and Biotechnology, Jan. 13, 2016, vol. 100, pp. 2121-2132 (2016).
Whitford W., et al., "Continuous Production of Exosomes Utilizing the Technical Advantages of Hollow-Fiber Bioreactor Technology." Genetic Engineering and Biotechnology News Sep. 15, 2015 (2015) vol. 35, Nr.16, pp. 1-2.
Abstract Book: ISEV2017 (2017), Journal of Extracellular Vesicles, May 2017. p. 207.IP.08, DOI: 10.1080/20013078.2017.1310414, 1 pg.
JP Patent Office, Notice of Reasons for Rejection, Application No. 2020-514492, Mail date Jun. 27, 2022, 11 pgs with translation.
European Patent Office, European Communication, Supplementary European Search Report, Application No. 18854201.3, Applicant Symbiocelltech, LLC, Mail Date Apr. 28, 2021, 9 pages.
Westenfelder, Christof et al., Durable Control of Autoimmune Diabetes in Mice Achieved by Intraperitoneal Transplantation of "Neo-Islets," Three-Dimensional Aggregates of Allogenic Islet and "Mesenchymal Stem Cells" " MSC-Rich Neo-Islets Control Autoimmune T1DM," Stem Cells Translational Medicine, vol. 6, No. 7, May 3, 2017, pp. 1631-1643, XP055536369, US, ISSN: 2157-6564, DOI: 10.1002/sctm.17-0005.
Westenfelder, Christof, "Human Mesenchymal Stem Cells Cultured in a Hollow Fiber Bioreactor Maintain Constant Levels of Exosomes in the Perfusion Medium: Relevance to the Simultaneous Production of Two Biotherapeutic A," Kidneyweek 2020; Bioengineering Abstract P00297, Oct. 22, 2020, XP055796522, Retrieved from the Internet: URL: https://www.asn-online.org/education/kidneyweek/ 2020/program-abstract.aspxcontrolId=3443576, retrieved on Apr. 19, 2021, 3 pgs.

(Continued)

*Primary Examiner* — Gyan Chandra
(74) *Attorney, Agent, or Firm* — Patent Law Works LLP

(57) ABSTRACT

Disclosed herein is a method of generating exosomes (extracellular nanovesicles) and/or neo-islets from mesenchymal or adipose stem cells or islets, or other cells in a Hollow-Fiber-based Cell Expansion (HFCE) System. Such exosomes and/or neo-islets may be used for the treatment of T1DM, T2DM, or associated microvascular disease.

7 Claims, 2 Drawing Sheets

(56) References Cited

OTHER PUBLICATIONS

De Souza, Bianca Marmontel, et al., Effect of co-culture of mesenchymal stem/stromal cells with pancreatic islets on viability and function outcomes: a systematic review and meta-analysis. Islets, (2017) 9(2), 30-42. https://doi.org/10.1080/19382014.2017.1286434.

Eghbali, Hadis, et al., Hollow Fiber Bioreactor Technology for Tissue Engineering Applications. International Journal of Artificial Organs, (2016) 39(1), 1-15. https://doi.org/10.5301/ijao.5000466.

Gundersen, Sharon, et al., Hemoglobin regulates the metabolic and synthetic function of rat insulinoma cells cultured in a hollow fiber bioreactor. Biotechnology and Bioengineering, (2010) 107(3), 582-592. https://doi.org/10.1002/bit.22830.

Hoesli, Corinne A., et al., A novel alginate hollow fiber bioreactor process for cellular therapy applications. Biotechnology Progress, (2009) 25(6), 1740-1751. https://doi.org/10.1002/btpr.260.

JP Patent Office, Notice of Reasons for Rejection, Application No. 2022-208535, Mail date Dec. 11, 2023, 8 pgs with translation.

Shipley, R.J., et al., A strategy to determine operating parameters in tissue engineering hollow fiber bioreactors. Biotechnology and Bioengineering, (2011) 108(6), 1450-1461. https://doi.org/10.1002/bit.23062.

Vaithilingam, Vijayaganapathy, et al., Co-encapsulation and co-transplantation of mesenchymal stem cells reduces pericapsular fibrosis and improves encapsulated islet survival and function when allografted. Scientific Reports, (2017) 7(1), 10059-13. https://doi.org/10.1038/s41598-017-10359-1.

\* cited by examiner

ADAPTATION OF HOLLOW-FIBER-BASED CELL CULTURE TECHNOLOGY FOR THE MANUFACTURING OF (1) NEO-ISLETS, EMPLOYED FOR THE TREATMENT OF TYPE 1 AND TYPE 2 DIABETES MELLITUS, AND (2) THE GENERATION OF EXOSOMES FROM VARIOUS CELL TYPES, USED IN THE TREATMENT OF DIFFERENT ORGAN INJURIES AND DISEASES

FIELD

This disclosure relates generally to the fields of cell biology and medicine. In particular this disclosure relates to the production of cells and exosomes for use in treating subjects and more particularly to the production of cells and exosomes that are useful in treating Diabetes mellitus

BACKGROUND OF THE INVENTION

Mesenchymal Stem or Stromal Cells (MSC) from bone marrow, fat, umbilical cord, placenta, amniotic fluid, and other sources are non-embryonic, "adult" stem cells that possess potent anti-inflammatory, anti-apoptotic, mitogenic, angiogenic and vasculo-protective, immune modulating, anti-fibrotic, anti-thrombotic and anti-biotic paracrine activities that have been used for the promising treatment of various acute and chronic diseases and organ injuries. Most specifically, we have shown (Westenfelder C, Gooch A. et al. STEM CELLS Translational Medicine Volume 6, Issue 7, pages 1631-1643 July 2017) that the co-aggregation of allogeneic MSCs and allogeneic, culture expanded pancreatic islet cells durably corrects T1DM in a mouse model of auto-immune T1DM that closely resembles human and canine T1DM (NOD mice). The MSC component of NIs provides robust protection against allo- and auto-immune attacks of insulin-producing endocrine islet cells in vivo, making the use of potentially toxic anti-rejection drugs unnecessary, as these can cause serious infections, malignancies, damage of transplanted islets in the liver and kidney disease. In addition, the NI technology allows the generation of 80+ therapeutic doses from one pancreas donor, which is in striking contrast to pancreatic islet transplantation protocols, where a diabetic recipient needs 4 or more donors for one single treatment. MSCs in culture release beneficial cytokines and growth factors that mediate their pleiotropic effects. In addition, MSCs, like essentially all cells, release Exosomes (30-100 nm in diameter) into their microenvironment that are taken up by adjacent cells, which, in turn, results in paracrine signaling in the target cells. Signaling occurs by the lateral transfer of mRNAs, miRNAs, proteins, and lipids, which together are known to exert beneficial effects that are essentially identical to those of intact MSCs.

BRIEF SUMMARY OF THE INVENTION

Described herein are a) mesenchymal and/or adipose stem cells; b) pancreatic islet cells; c) mesenchymal and/or adipose stem cell-derived exosomes; and d) exosomes derived from other cell types such as endothelial, muscle and other cultured cells.

Further described are Neo-Islets (NIs), where NIs comprise mesenchymal and/or adipose stem cells; and pancreatic islet cells.

Disclosed herein is a method of generating exosomes (extracellular nanovesicles). Such methods may include the expansion of mesenchymal or adipose stem cells or islets, or other cells in a Hollow-Fiber-based Cell Expansion (HFCE) System and collecting exosomes released by the culture expanded mesenchyma, adipose stem cells, or other cells from the HFCE System.

In embodiments of the method, the cells are expanded to 70-95% confluency. In further embodiments, the culture medium perfused through the HFCE system may be adjusted to enhance the release of exosomes into the lumens of the hollow fibers.

Embodiments include exosomes produced by such methods as well as methods of treating subjects suffering from T1DM, T2DM, or associated microvascular disease by treating the subject with the exosomes produced by the above methods. In particular embodiments the exosomes have been cryopreserved for at least two years prior to treatment.

Provided are embodiments of a method for generating Neo Islets. Particular embodiments include culture expanding mesenchymal or adipose stem cells and pancreatic islet cells in HFCE System and collecting Neo Islets from the HFCE System. In embodiments of the method, the cells are expanded to 70-95% confluency.

In embodiments the Neo Islets may comprise a) dedifferentiated islet cells and mesenchymal or adipose stem cells and/or redifferentiated islet cells and mesenchymal or adipose stem cells. In particular embodiments wherein the islet cells and stem cells are present in the Neo Islets at an islet cell:stem cell ratio of about 1:100, 1:75, 1:50, 1:25, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 25:1, 50:1, 75:1, or 100:1.

In certain embodiments the collected Neo Islets are placed in a hydrogel and/or are encapsulated.

Embodiments include neo-islets produced by such methods.

Embodiments include methods of treating a subject suffering from T1DM or T2DM, and associated microvascular disease with neo-islets produced by the above described methods.

Also described are methods of treating a subject with T1DM or T2DM, the methods comprising: administering to the subject NIs with or without exosomes derived from MSCs or other cultured cells.

The here disclosed NI technology harnesses the pleiotropic functions of MSCs, where appropriate, and of their Exosomes where needed in order to repair and protect the affected capillary system in the diseases and disorders listed above.

"Treating" or "treatment" does not require a complete cure. It means that the symptoms of the underlying disease are at least reduced, and/or that one or more of the underlying cellular, physiological, or biochemical causes or mechanisms causing the symptoms are reduced and/or eliminated. It is understood that reduced, as used in this context, means relative to the state of the disease, including the molecular state of the disease, not just the physiological state of the disease.

As used herein "therapeutically effective amount" is an amount sufficient to act as a treatment as defined above. This may be determined by, e.g., standard techniques used to monitor and/or diagnose a particular disease state.

As used herein, "comprising," "including," "containing," "characterized by," and grammatical equivalents thereof are inclusive or open-ended terms that do not exclude additional, unrecited elements or method steps, but also includes the more restrictive terms "consisting of" and "consisting essentially of."

In conclusion, the purpose of using a customized Hollow-Fiber-based Cell Culture system is to allow the scaled-up and highly efficient production of MSCs, islet cells and thus NIs for the treatment of diabetes. In addition, various cultured cell types in a Hollow-Fiber-based Cell Culture system can be programmed to generate large numbers of Exosomes in which therapeutically desired and unique therapeutic qualities are potentiated and used for the treatment of specific diseases in Personalized and Regenerative Medicine. It is also envisioned that the broad scale use of the developed, high efficiency Hollow-Fiber-based Cell Culture Technology will prove cost saving for the entire Health Care System.

BRIEF DESCRIPTION OF THE DRAWINGS

FIG. 3A depicts a schematic representation of the generation of neo-islets from mouse MSCs and mouse islet cells. FIG. 3B provide micrographs of neo-islets derived from mouse, canine, and human cells.

DETAILED DESCRIPTION OF THE INVENTION

Figures 1, 2:
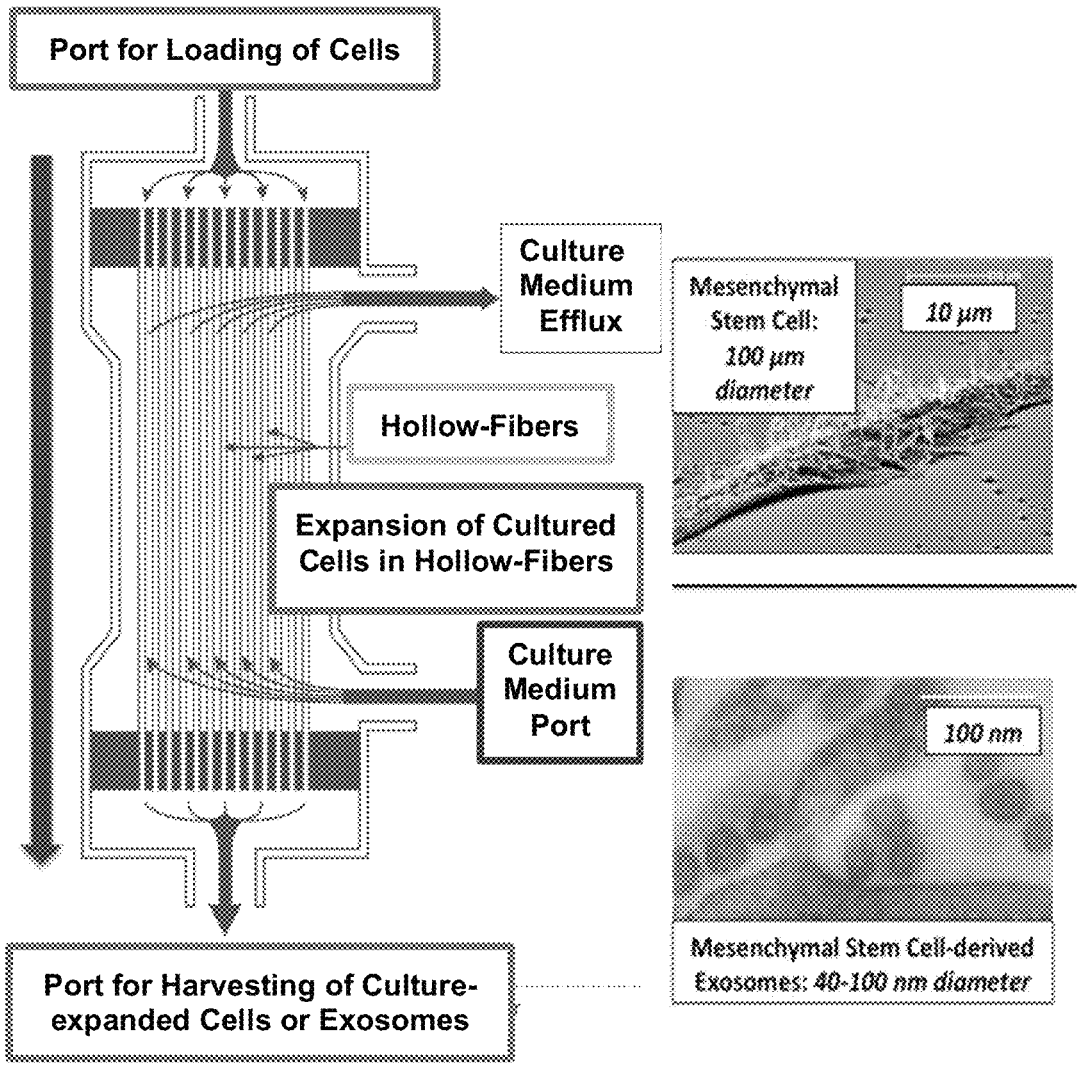
FIG. 1. Schematic representation of a Hollow-Fiber-based Cell Expansion (HFCE) System.
FIG. 2. Micrographs of a mesenchymal stem cell and mesenchymal stem cell-derived exosomes.
Figure 3:
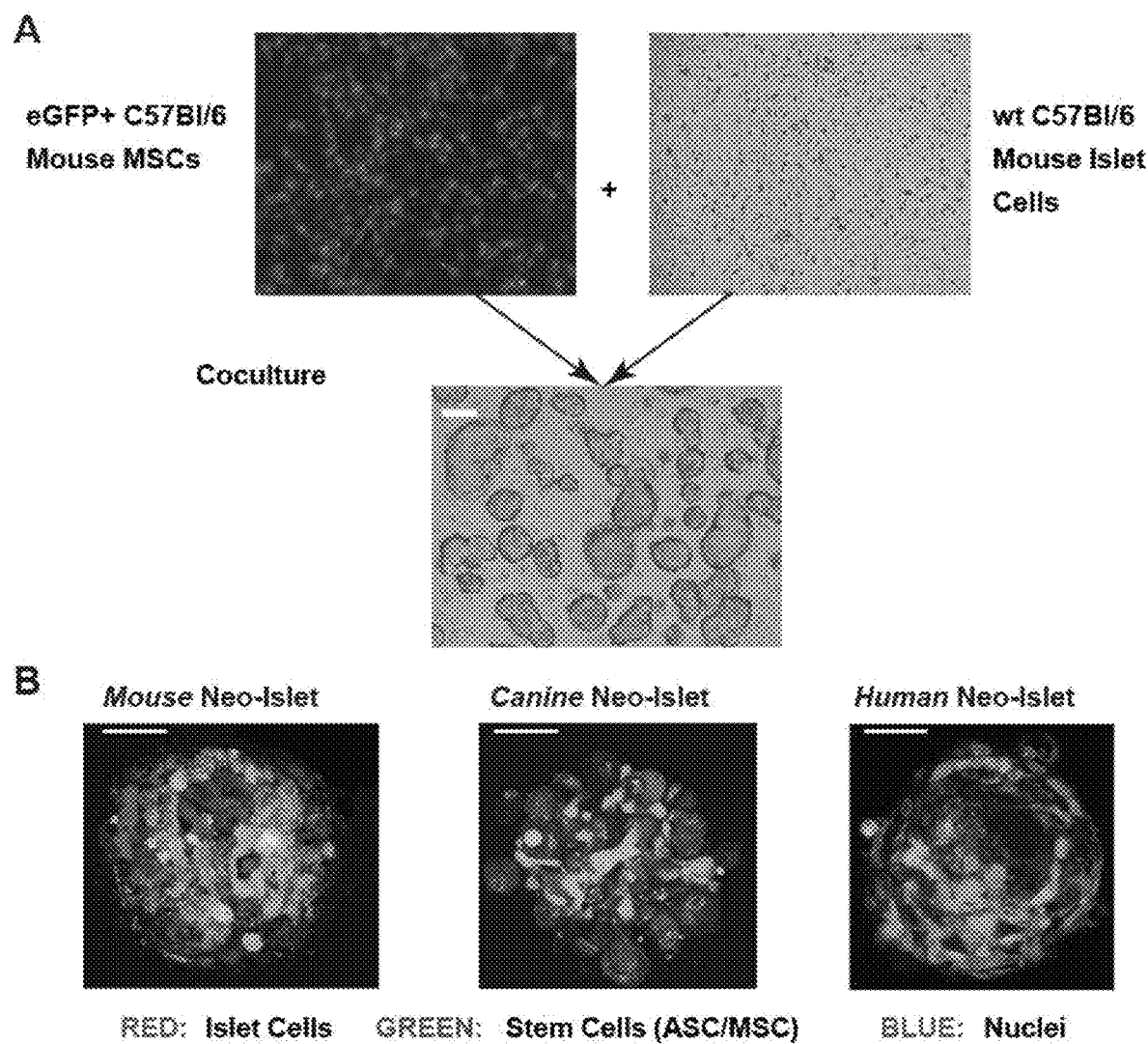
FIGS. 3A and 3B.

The illustrations presented in this disclosure are not meant to be actual views of any particular compositions, but are merely representations employed to describe illustrative embodiments. Thus, the figures are not necessarily to scale.

In this disclosure, the term Mesenchymal Stem Cell means and includes mesenchymal and/or adipose stem cells; and b) mesenchymal and/or adipose stem cell-derived exosomes.

While certain illustrative embodiments have been described in connection with the figures, those of ordinary skill in the art will recognize and appreciate that the scope of this disclosure is not limited to those embodiments explicitly shown and described in this disclosure. Rather, many additions, deletions, and modifications to the embodiments described in this disclosure may be made to produce embodiments within the scope of this disclosure, such as those specifically claimed, including legal equivalents. In addition, features from one disclosed embodiment may be combined with features of another disclosed embodiment while still being within the scope of this disclosure, as contemplated herein.

This disclosure relates generally to the manufacturing of Neo-Islets for the treatment of Type 1 Diabetes mellitus in companion animals such as dogs and in human subjects. Neo-Islets (NIs) are co-aggregates of culture expanded pancreatic islet cells and cultured Mesenchymal Stem Cells (MSCs) obtained from bone marrow or adipose tissue. The Hollow-Fiber-based Cell Culture technology is a highly efficient, enclosed system, therefore not requiring a clean room that is currently used for the expansion of attached MSCs and other cells both for research and clinical use and for suspension culture of various types of blood cells.

Therapeutic targets for the here disclosed technology include both Type 1 and Type 2 Diabetes mellitus and their multiorgan complications (kidneys, eyes, heart, neurological and others), vasculitides, auto-immune diseases, sepsis, acute and chronic kidney diseases, cardiovascular and neurological diseases, solid organ transplantation, vascular rejection, wound healing, atherosclerosis, aging, and various degenerative retinal and neurological diseases. More specifically, disclosed embodiments relate to the therapeutic use of Mesenchymal Stem Cells from various sources as a critical component of NIs and their Exosomes, to repair and protect and stabilize the diseased microvasculature and thereby improve outcomes and survival both in canines and humans with T1DM.

It is envisioned that a Hollow-Fiber-based Cell Culture (HFCE) system can be used, with modifications, for the expansion of islet cells, the formation of therapeutic doses of NIs, and the generation of Exosomes from cultured MSCs and other cells that are programmed to impart specific therapeutic characteristics on released Exosomes for the treatment of various diseases, such as acute renal failure, chronic kidney disease, strokes, heart attacks, various auto-immune diseases, organ transplantation, and others The use of an HFCE system to produce exosomes and NIs: (See also above paragraph). Such HFCE systems are in some aspects similar to the configuration of clinically used hemodialysis cartridges. These systems have the distinct advantage of providing a highly favorable surface area to culture medium ratio and flexibility regarding changes in culture conditions of both attached cells (e.g. Mesenchymal Stem, islet, and other cell types) and cells in suspension culture, a technique that is used for the manufacturing of Neo-Islets. In addition, various attached cell types that are expanded in a HFCE system can be programmed to release exosomes with optimized therapeutic characteristics such as immune-isolation, anti-inflammatory, cytoprotective, angiogenic, and others. Together, the efficacy and therefore costs of cell culturing, Neo-Islet and exosomes production in a suitable HFCE system, are expected to be substantially more favorable than in conventional culture systems.

Production of Exosomes (extracellular nanovesicles) are spontaneously released from MSC, ASC and most other cell types when efficiently cultured in a suitable HFCE System (a bioreactor) or flask system. They can be continuously harvested, characterized (surface marker expression, miRNA, RNA, DNA, peptides, cytokines and lipid cargo), cryopreserved or freshly used. The utilized cell culture media in the HFCE System are standard media that are used by all experts in the field. However, modifications of the culture media can be employed to generate exosomes that possess desirable, therapeutic characteristics, such as augmented anti-inflammatory, immune-modulating and trophic effects (anti-apoptotic, mitogenic, angiogenic and others).

The production of NIs with a HFCE System, as described above, utilizes culture expanded pancreatic islet cells (insulin, glucagon, somatostatin, PPY producing cells and other non-endocrine cells) and culture expanded MSCs or ASCs. The suspension co-culture of islet cells and MSCs or ASCs in a suitably modified HFCE System results in the efficient generation of NIs that, after appropriate characterization (relevant gene expression profiles, glucose-sensitive insulin release test, etc.) can be used fresh for the treatment of T1DM or they can be cryopreserved for later use.

Regarding the treatment of subjects using NIs, the contents of U.S. application Ser. No. 15/261,750 are incorporated herein in its entirety by this reference.

EXAMPLES

The following examples are provided for illustration purposes only and are not to be construed as limiting the disclosure to the embodiments specifically disclosed therein.

Both type 1 and type 2 diabetes mellitus progressively result in wide-spread end organ damage, affecting the retina, coronaries, the nervous system, kidneys and other organs though microvascular disease that injures the capillary beds in these organs through endothelial and pericytes dysfunction, microvascular obstruction and inflammation, vasoconstriction, vascular leakage, coagulopathy, and fibrosis. This microvascular damage also affects the capillaries of the islets of Langerhans in the pancreas. This pathomechanisms, we hypothesized could accelerate the destruction of insulin producing cells and thereby hasten the complete loss of intrinsic insulin production, i.e., greatly aggravate the diabetic state in a patient. Accordingly, we tested whether the parenteral administration of mesenchymal and/or adipose-derived exosomes to db/db mice with advanced diabetic disease would improve glycemic control. This was observed, together with improvement in diabetic kidney disease.

In analogy to the microvascular disease of diabetes, which shares most pathologic features of various vasculitides, auto-immune diseases, sepsis, acute and chronic kidney diseases, cardiovascular and neurological diseases, solid organ transplantation, vascular rejection, wound healing, atherosclerosis, aging, and various degenerative retinal diseases, we expect that the treatment with Mesenchymal and/or Adipose Stem Cells alone or their exosomes alone or in combination with their parent stem cells will favorably affect outcomes in this large group of microvascular diseases.

A type 2 diabetic male subject presents with chronic kidney disease. MSCs are isolated from the subject and expanded in culture. The expanded MSCs are administered to the subject in an amount sufficient to improve the symptoms from which the subject is suffering that are related to microvasculature issues.

Detailed Examples of Using an HFCE System to Produce Exosomes and NIs

It is envisioned that the HFCE System is used to produce exosomes from cultured MSCs, ASCs, and other cells of interest as shown in FIG. 1. The cells of interest from which exosomes (MSCs or ASCs, other cells) or NIs (islet cells, MSCs or ASCs) are produced will be loaded, suspended in suitable culture media, into the top port (FIG. 1). Defined culture media will perfuse the internal and external spaces of the hollow fibers that contain cells to be expanded or co-cultured (MSCs or ACSs with islet cells). Once the desired degree of cell expansion within the HFCE System is reached, cells are detached and harvested, at the bottom of the HFCE System. Once the desired degree of cell clustering is reached, NIs are harvested at the bottom of the HFCE System. Exosomes from cultured cells are collected without detaching the cultured cells.

The treatment of diabetic (Type 1) subjects with the NIs consists of administering a body weight-based dose of this composition into the intraperitoneal space of such a subject, using ultrasound guidance and local anesthesia. The Exosome-based treatment of subjects with various diseases (autoimmune, transplantation-related complications, ischemic injury, vasculitis, liver disease, neurodegenerative, retinal, cardiac, renal and other disorders) consists on the intravenous administration of a predetermined dose of functionally "customized" (see above) Exosomes.

What is claimed is:

1. A method for generating Neo Islets, the method comprising:
    culturing expanding mesenchymal or adipose stem cells and pancreatic islet cells in a Hollow-Fiber-based Cell Expansion (HFCE) System;
    forming, in the HFCE system, Neo Islets from the cultured mesenchymal or adipose stem cells and pancreatic islet cells; and
    collecting the formed Neo Islets from the HFCE System.

2. The method according to claim 1 wherein the cells are expanded to 70-95% confluency.

3. The method according to claim 1, wherein the Neo Islets comprise:
    a) dedifferentiated islet cells and mesenchymal or adipose stem cells; or
    b) redifferentiated islet cells and mesenchymal or adipose stem cells.

4. The method according to claim 3, wherein the islet cells and stem cells are present in the Neo Islets at an islet cell:stem cell ratio of about 1:100, 1:75, 1:50, 1:25, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 25:1, 50:1, 75:1, or 100:1.

5. The method according to claim 1, wherein the collected Neo Islets are placed in a hydrogel.

6. The method according to claim 1, wherein the collected Neo Islets are encapsulated.

7. A method for generating Neo Islets, the method comprising:
    culturing expanding mesenchymal or adipose stem cells and pancreatic islet cells in a Hollow-Fiber-based Cell Expansion (HFCE) System;
    collecting exosomes from the HFCE System;
    forming, in the HFCE system, Neo Islets from the cultured mesenchymal or adipose stem cells and pancreatic islet cells; and
    collecting the formed Neo Islets from the HFCE System.

* * * * *